United States Patent [19]

Lottick

[11] 4,370,980

[45] Feb. 1, 1983

[54] ELECTROCAUTERY HEMOSTAT

[76] Inventor: Edward A. Lottick, 789 Wyoming Ave., Kingston, Pa. 18704

[21] Appl. No.: 242,746

[22] Filed: Mar. 11, 1981

[51] Int. Cl.³ .............................................. A61B 17/38
[52] U.S. Cl. ................................. 128/303.17; 128/325
[58] Field of Search ...................... 128/303.13–303.19, 128/321, 800, 801, 325; 200/157, 282, 295, 338; 219/240

[56] References Cited

U.S. PATENT DOCUMENTS

| 2,002,594 | 5/1935  | Wappler      | 128/303.14 X |
| 2,120,598 | 6/1930  | Beuoy        | 219/240 X    |
| 2,176,479 | 10/1939 | Willis       | 128/303.13   |
| 3,100,489 | 8/1963  | Bagley       | 128/303.17   |
| 3,643,663 | 2/1972  | Sutter       | 128/303.17   |
| 3,801,766 | 4/1974  | Morrison, Jr.| 200/157      |
| 3,878,348 | 4/1975  | German       | 200/157      |
| 3,911,241 | 10/1975 | Jarrard      | 128/303.17 X |
| 4,005,714 | 2/1977  | Hiltebrandt  | 128/303.17   |
| 4,041,952 | 8/1977  | Morrison, Jr.| 128/303.13   |
| 4,076,028 | 2/1978  | Simmons      | 128/303.13   |

FOREIGN PATENT DOCUMENTS

| 757933  | 1/1934  | France   | 128/303.14 |
| 1536272 | 6/1967  | France   | 128/303.17 |
| 575103  | 10/1977 | U.S.S.R. | 128/303.14 |
| 578972  | 11/1977 | U.S.S.R. | 128/303.14 |

OTHER PUBLICATIONS

Stevenson, "Combined Diethermy Forceps and Scissors", The Lancet, pp. 650–651, 10/24/59.

Primary Examiner—Lee S. Cohen
Attorney, Agent, or Firm—Michael F. Petock

[57] ABSTRACT

An electrocautery hemostat is provided which may be used as a hemostatic clamping device and an apparatus for cauterizing bleeding blood vessels during surgery. The electrocautery hemostat is comprised of a pair of pivoted members which form at one end mating jaws for enabling the clamping of a bleeding blood vessel. The opposite ends of the members are provided with an insulative covering with at least one opening therethrough. An electrical switch is provided for clamping to one of the pivoted members and for making an electrical connection to the member through the opening in the insulative covering. The other end of the switch is connected through an electrical conductor to a source of electrical energy. The mating jaws are of a smaller cross-section than a conventional hemostat and are adapted for use in probing and cauterizing. The device of the present invention may be used by a surgeon with one hand, the other hand being free to perform other functions, both as a cauterizing instrument and to clamp, as may be necessary, a bleeding blood vessel in a manner similar to that of a hemostat.

8 Claims, 7 Drawing Figures

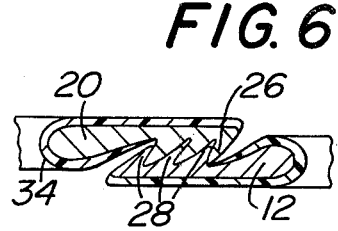
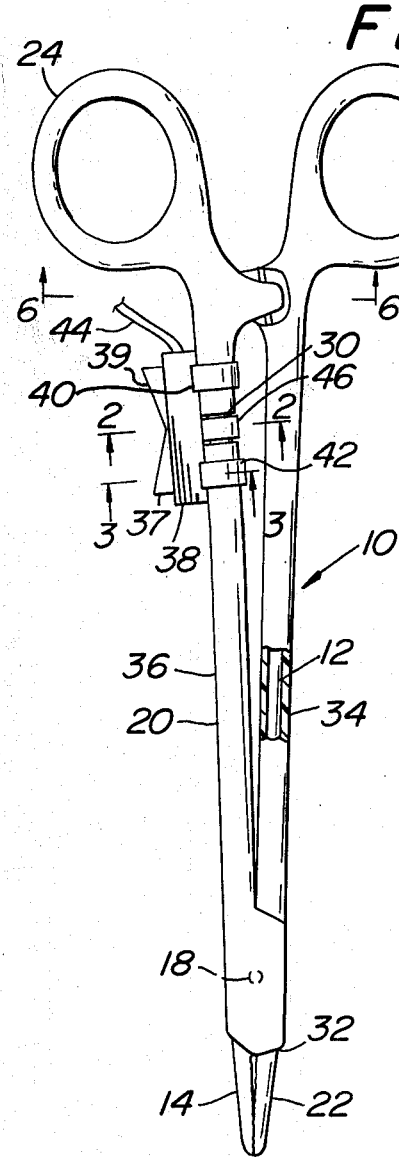
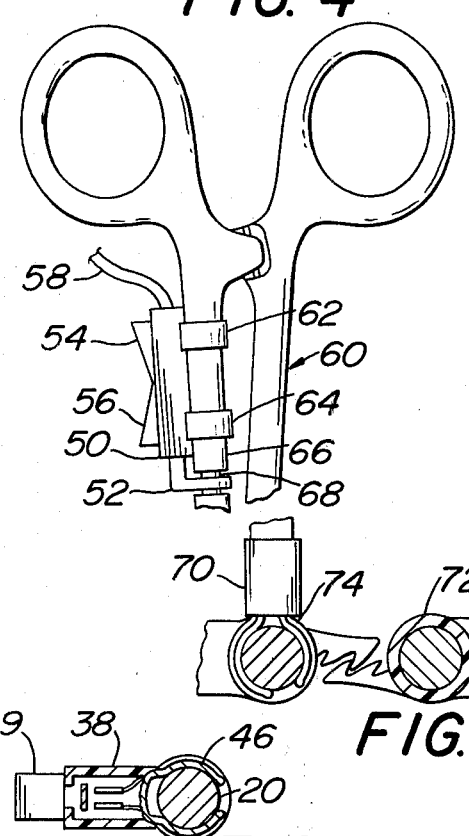
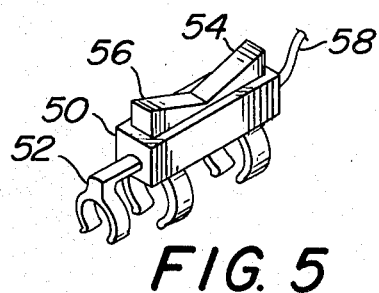
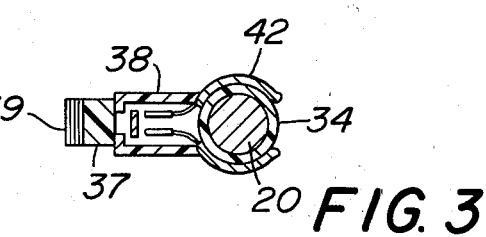

ELECTROCAUTERY HEMOSTAT

BACKGROUND OF THE INVENTION

The present invention is directed to an apparatus which provides both electrocautery and hemostatic clamping functions. More particularly, the present invention is directed to an electrocautery and hemostatic clamping device which may be utilized in an advantageous manner by a surgeon during the performance of surgery providing increased control of bleeding with one hand while allowing the surgeon's second hand to remain free for other functions.

Surgery has been performed for many years. Control of bleeding during surgery is a most important consideration and is a function which can consume a fair amount of time during the surgical procedure if proper instruments are not available. The hemostat, a clamping device, has been available for many years. Years ago, the bleeding vessel had to be clamped and then ligated or tied off with suture material.

Some years ago, the control of bleeding by applying an electrical current to the cut bleeding blood vessel became popular. Such electrocautery is advantageous because it is fast and can be used not only on bleeding blood vessels, but also on oozing areas that could previously only be sponged. However, frequently, the application of the electrocautery device fails to cauterize and stop the bleeding from a bleeding blood vessel, sometimes referred to as a "bleeder". This is especially true in the case of larger blood vessels, and it may be necessary to pluck the bleeder from the incision with a hemostat and then apply an electrocautery instrument to the bleeder. Plucking the bleeder from the incision tends to isolate the bleeder from the surrounding tissue and removes it from its surrounding pool of blood. The pool of blood surrounding the tissues diffuses the electric current and render it ineffective. Clutching the bleeder with a hemostat, dabbing and applying the electrocautery instrument, however, requires at a minimum the two hands of the surgeon and at least one assisting hand.

Electrocautery instruments are known in the prior art. The prior art also discloses electrocautery devices combined with forceps, for example, see U.S. Pat. Nos. 3,100,489; 3,643,663; 4,005,714 and 4,076,028. However, these electrocautery instruments utilize forceps. Forceps are practically never used to pick up a bleeder. Sharp tipped forceps can poke holes in tissue causing more bleeding. Forceps or tweezers are cumbersome to use. U.S. Pat. No. 3,100,489 discloses a tweezers type electrocautery device which requires that the tongs be held together in order to have current flow through the tip. Furthermore, so long as the forcep arms are held together, the current is continually applied to the tissue, which may cause burning or singing of the tissue.

U.S. Pat. No. 4,041,952 attempts to remedy some of the defects as aforesaid. However, the forceps still maintain the sharp tips which tend to cause more bleeding. Furthermore, there is no means of retaining a clamping action on a bleeding blood vessel. Furthermore, the switch and arrangement are not readily adaptable for use with one hand during surgery.

SUMMARY OF THE INVENTION

In accordance with the present invention, a modified hemostat and an electrocautery instrument are combined wherein both the hemostatic clamping function and the electrocautery function may be conveniently operated with the one hand of the surgeon. The surgeon can either point the tip of the instrument and energize the electrocautery instrument to cauterize a bleeding blood vessel or the surgeon may pluck the vessel from the incision and then cauterize it. In this manner, his one hand has control of both the probe or pluck decision as well as the subsequent cauterization. Therefore, his other hand is free for dabbing the field clear of bleeding.

In accordance with the present invention, the switch mechanism may be conveniently located on the instrument. The jaws of the instrument allow a clamping action and do not have sharp tips which may puncture additional tissue in attempts to pluck a bleeding blood vessel from the surgical field. The instrument of the present invention may be conveniently operated particularly in view of the ring structure of the handles, wherein the thumb and ring finger of the surgeon may be placed through the rings and the switch operated by the surgeon's index finger on the same hand.

Briefly, in accordance with the present invention, an electrocautery and hemostatic clamping device are provided. A first and second pivoted members are pivoted at a point between the ends of the members. The first and second pivoted members are provided with mating jaws at one end. The mating jaws are of a cross-section smaller than a conventional hemostat and are adapted for probing during the performance of surgery. The first and second members are provided with handles or rings that are near the end opposite the jaws. An adjustable retaining means is provided for retaining the jaws in a predetermined clamped position. An insulative covering is applied over the first and second members extending substantially from the point of pivot to the handle end of the members. At least one opening is provided through the insulative covering for an electrical connection to one of the members. An electrical switch is adapted to clamp over the insulative coating of one of the members. The electrical switch is provided with means for connecting to an electrical source of energy and an electrical connector for connecting to said member through the opening in the insulative coating. The electrical switch may be operated to apply an electrical potential to the member for cauterizing.

BRIEF DESCRIPTION OF THE DRAWINGS

FIG. 1 is a side elevation view showing an electrocautery instrument in accordance with the present invention.

FIG. 2 is a cross-sectional view through FIG. 2 along line 2—2.

FIG. 3 is a cross-sectional view through line 3—3 of FIG. 1.

FIG. 4 is a side elevation view of a portion of another embodiment of an electrocautery hemostat in accordance with the present invention.

FIG. 5 is a perspective view of a switch means utilized in the alternate embodiment of FIG. 4.

FIG. 6 is cross-sectional view taken along line 6—6 of FIG. 1.

FIG. 7 is a cross-sectional view showing a preferred mounting of a switch means out of the plane formed by the members and handles of the instrument.

DETAILED DESCRIPTION OF THE PREFERRED EMBODIMENTS

Referring now to drawings in detail wherein like numerals indicate like elements, there is shown in FIG.

1 an electrocautery hemostat device in accordance with the present invention wherein the instrument or device 10 is comprised of a first member 12 provided with a jaw portion 14 at one end and a ring handle portion 16 at its other end. Member 12 is pivotally mounted at 18 to a second member 20 having a jaw portion 22 at one end and a ring handle 24 at its opposite end. Instrument 10 is shown with mating jaws 14 and 22 in a clamped position wherein an interlocking tooth 26 on member 20 mates with one of a plurality teeth 28 on element 12 as shown in FIG. 6.

Members 12 and 20 are provided with an insulative covering applied over the length of the members extending from around the pivot point 18 to and over ring handles 16 and 24 except for an opening 30 therethrough for an electrical connection to be discussed hereinafter. As illustrated in FIG. 1, in a preferred embodiment, the insulative covering may extend slightly beyond the pivot point 18, substantially to the jaws ending at 32. Instrument 10 may be coated by an insulative covering by dipping the member into a liquid solution of insulative coating material which then hardens, such as latex. Alternatively, the insulative coating 34 may extend only to a point midway along the length of member 12 and 20, just sufficient to protect the surgeon from any inadvertent electrical shock, therefore, the insulative coating 34 may end in the area of 36. However, as illustrated, the insulative coating may preferably extend down to the area of the pivot connection between members 12 and 20.

An electrical switch 38 is provided with a clamp over the insulative coating on member 20 by means of mechanical clamps 40 and 42. The clamping of member 42 of switch 38 over the insulative coating 34 of member 20 may be seen in greater detail in FIG. 3. Switch 38 is connected to an electrical source of energy through electrical conductor 44. Electrical energy may be applied through switch 38 and electrical connector 46 to member 20 and instrument 10. The electrical connection by means of electrical connector 46 to switch 38 to member 20 is shown in greater detail in FIG. 2. Preferably, switch 38 is a double switch which has different amounts of resistance in series with the respective contacts 37, 39 of the two switches thereby enabling different amounts of current flow to be applied through the tissue as desired by the surgeon.

Referring now to FIG. 4, there is shown an alternate embodiment of the present invention wherein a switch 50 is clamped to an instrument 60 by means of mechanical connectors 62 and 64. Mechanical connectors 62 and 64 are applied over the insulative coating 66. Electrical switch 50 is provided with an electrical connector 52 which projects from one end of switch 50 and connects with metallic member 68, which is preferably stainless steel. Electrical switch 50 is provided with double switches 54 and 56 similar to switch 38. Switch 50 is connected to a source of electrical energy through electrical conductor 58. A perspective view of switch 50 is shown in FIG. 5 disconnected from instrument 60.

Another alternate embodiment of the present invention is illustrated in FIG. 7 wherein a single switch 70 is mounted out of the plane formed by members 72 and 74, which correspond to members 12 and 20 of the embodiment of FIG. 1. In other words, switch 70 is positioned at approximately 90 degrees to the plane formed by the centers of members 72 and 74. It is believed that many surgeons would actually prefer this positioning of switch member 70. Switch member 70 may preferably be mounted sufficiently distant from the handle to permit convenient operation of the switch by the index finger of the surgeon. Switch 70 may be a single throw switch utilized solely for cauterization, or may be a switch similar to switch 38 which has two sets of contacts, one for cauterization and the other for cutting.

In both of the embodiments disclosed herein, the electrical switch may be readily removed from the instrument. The electrical switch merely snaps onto the member making electrical connection with it through its electrical connector.

The present invention may be embodied in other specific forms without departing from the spirit or essential attributes thereof and, accordingly, reference should be made to the appended claims rather than to the foregoing specification as indicating the scope of the invention.

I claim:

1. An electrocautery and hemostatic clamping device, comprising:

a first and second pivoted members pivoted at a point between the ends of said members, said members being comprised of a conductive material;

said first and second pivoted members being provided with mating jaws at one end, said mating jaws being of a cross-section adapted for probing during the performance of surgery;

said first and second members being provided with handle means at a predetermined distance from the jaws and adjustable retaining means for retaining said jaws in a predetermined clamping position;

an insulative covering applied over said first and second members extending substantially from the point of pivot to said handle means with at least one opening therethrough for an electrical connection to one of said members; and electrical switch means adapted to be releasably attached to one of said members, said electrical switch means being provided with means for being connected to an electrical source, said electrical switch means being provided with an electrical connector for connecting through said opening in said insulative covering of said member to which said electrical switch means is attached whereby through operation of said electrical switch means an electrical potential may be applied to said members for cauterizing.

2. An electrocautery and hemostatic clamping device in accordance with claim 1 wherein said insulative covering is comprised of latex.

3. An electrocautery and hemostatic clamping device in accordance with claim 1 wherein said electrical switch means is provided with a first and a second switch, each being operable to connect a different predetermined amount of resistance in series with the electrical source.

4. An electrocautery and hemostatic clamping device in accordance with claim 1 wherein said electrical connector is mounted to a housing of said electrical switch means intermediate its ends.

5. An electrocautery and hemostatic clamping device in accordance with claim 1 wherein said electrical connector of said electrical switch means is mounted to a housing of said electrical switch means such that it extends from said housing in the longitudinal axis of said pivoted members.

6. An electrocautery and hemostatic clamping device in accordance with claim 1 wherein said handle means is comprised of ring shaped elements, each of which is adapted to receive at least one finger of a surgeon.

7. An electrocautery and hemostatic clamping device in accordance with claim 1 wherein said electrical switch means is clamped over one of the insulation covered members in such a manner that an operating button of said electrical switch means projects in a direction substantially perpendicular to the plane passing through the centers of said members.

8. An electrocautery and hemostatic clamping device in accordance with claim 1 wherein said electrical switch means is releasably attached to one of said members by a snap on mechanical clamp.

* * * * *